United States Patent
Khopade et al.

(10) Patent No.: US 8,778,364 B2
(45) Date of Patent: *Jul. 15, 2014

(54) NANODISPERSION OF A DRUG AND PROCESS FOR ITS PREPARATION

(75) Inventors: Ajay Jaysingh Khopade, Baroda (IN); Natarajan Arulsudar, Baroda (IN); Subhas Balaram Bhowmick, Baroda (IN)

(73) Assignee: Sun Pharma Advanced Research Company Ltd., Mumbai (IN)

(*) Notice: Subject to any disclaimer, the term of this patent is extended or adjusted under 35 U.S.C. 154(b) by 0 days.

This patent is subject to a terminal disclaimer.

(21) Appl. No.: 13/378,758

(22) PCT Filed: Jun. 18, 2010

(86) PCT No.: PCT/IN2010/000423
§ 371 (c)(1),
(2), (4) Date: Dec. 19, 2011

(87) PCT Pub. No.: WO2010/146606
PCT Pub. Date: Dec. 23, 2010

(65) Prior Publication Data
US 2012/0087959 A1    Apr. 12, 2012

(30) Foreign Application Priority Data
Jun. 19, 2009   (IN) .................. 1468/MUM/2009

(51) Int. Cl.
*A61K 9/00*   (2006.01)
*A61K 38/13*   (2006.01)
*A01N 37/10*   (2006.01)

(52) U.S. Cl.
USPC .................. 424/400; 514/20.5; 514/543

(58) Field of Classification Search
None
See application file for complete search history.

(56) References Cited

U.S. PATENT DOCUMENTS

| | | | |
|---|---|---|---|
| 5,399,363 A | 3/1995 | Liversidge et al. |
| 6,017,948 A | 1/2000 | Rubinfeld et al. |
| 6,046,230 A | 4/2000 | Chung et al. |
| 6,294,192 B1 | 9/2001 | Patel et al. |
| 6,365,191 B1 | 4/2002 | Burman et al. |
| 6,537,579 B1 | 3/2003 | Desai et al. |
| 6,753,006 B1 | 6/2004 | Desai et al. |
| 2002/0058060 A1 | 5/2002 | Kan et al. |
| 2002/0192280 A1 | 12/2002 | Hunter et al. |
| 2003/0109575 A1 | 6/2003 | Lambert et al. |
| 2004/0005339 A1 | 1/2004 | Shojaei et al. |
| 2004/0092428 A1 | 5/2004 | Chen et al. |
| 2004/0234597 A1 | 11/2004 | Shefer et al. |
| 2005/0238673 A1 | 10/2005 | Augustine et al. |
| 2005/0288521 A1 | 12/2005 | Naidu et al. |
| 2006/0024374 A1 | 2/2006 | Gasco et al. |
| 2006/0188566 A1 | 8/2006 | Liversidge et al. |
| 2008/0138424 A1 | 6/2008 | Ryde et al. |
| 2009/0163574 A1 | 6/2009 | Kim et al. |
| 2010/0068251 A1 | 3/2010 | Ali et al. |
| 2010/0151037 A1 | 6/2010 | Jiang et al. |

FOREIGN PATENT DOCUMENTS

| | | |
|---|---|---|
| WO | 01/17546 A1 | 3/2001 |
| WO | 01/21174 A1 | 3/2001 |
| WO | 03/077882 A2 | 9/2003 |
| WO | 2004/039351 A2 | 5/2004 |
| WO | 2006/133510 A1 | 12/2006 |
| WO | 2007/069272 A2 | 6/2007 |
| WO | 2008/127358 A2 | 10/2008 |
| WO | 2008/144355 A2 | 11/2008 |

OTHER PUBLICATIONS

International Search Report for PCT/IN2010/000423, dated Nov. 18, 2010.
Lacko, A.G., et al., "High Density Licoprotein Complexes as Delivery Vehicles for Anticancer Drugs", 2002, Anticancer Research, pp. 2045-2049.
International Search Report of PCT/IN2008/000857 dated Jun. 26, 2009.

*Primary Examiner* — Michael G Hartley
*Assistant Examiner* — Sun Y Kim
(74) *Attorney, Agent, or Firm* — Sughrue Mion, PLLC

(57) ABSTRACT

A nanodispersion containing nanoparticles having a mean size less than 300 nm dispersed in a vehicle that includes a water miscible solvent and water. The nanoparticles contain one or more drugs, a polymer and a surfactant, and the surfactant includes a mixture of fatty acids or its salts and sterol or its derivatives or its salts.

10 Claims, No Drawings

NANODISPERSION OF A DRUG AND PROCESS FOR ITS PREPARATION

The present invention relates to a 'nanodispersion' of a drug and process for its preparation.

BACKGROUND OF THE INVENTION

There are number of pharmaceutical drugs that are poorly soluble or insoluble in aqueous solutions. Such drugs provide challenges in terms of having poor oral bioavailability or in terms of formulating them for drug delivery especially through the intravenous route. If a drug is intravenously administered, particles must be small enough to safely pass through capillaries without causing emboli. For intravenous administration, it is recognized as safe to administer drugs in the form of solution, emulsion, liposomes, nanodispersions and the like. Another requirement that should be met while formulating a drug delivery system especially for hydrophobic drugs is that the formulation should be physically stable with no substantial aggregation or crystallization of the drug or change in appearance of the formulation on storage at room temperature for desired period of time.

Certain drugs exhibit very poor solubility in water and in most pharmaceutically acceptable solvents thus limiting their administration to patients. For example, commercially available product is Torisel® injection which comprises temsirolimus and dehydrated alcohol (39.5% w/v), dl-alpha-tocopherol (0.075% w/v), propylene glycol (50.3% w/v), and anhydrous citric acid (0.0025% w/v), polysorbate 80 (40.0% w/v). After the TORISEL (temsirolimus) injection vial has been diluted with diluent the solution contains 35.2% alcohol. Yet another injectable available in the market comprising high amount of surfactant is Sandimmune® Injection (cyclosporine injection, USP) available in a 5 mL sterile ampoule for I.V. administration. Each mL contains: cyclosporine, USP 50 mg; *Cremophor® EL (polyoxyethylated castor oil) 650 mg; alcohol, Ph. Helv 32.9% by volume which must be diluted further with 0.9% Sodium Chloride Injection or 5% Dextrose Injection before use. Cremophor EL, a polyoxyethylated castor oil vehicle, and dehydrated ethanol USP (1:1, v/v) are used. Although these solvents systems are biologically and pharmacologically acceptable, they have known to have side effects, including acute hypersensitivity reactions and peripheral neuropathies. It may be noted that the use of solubilizers like Cremophor™ EL in large amounts lead to various adverse effects such as serious or fatal hypersensitive and hypertensive reactions, bradyarrhythmia, anemia, neutropenia and/or peripheral neuropathy.

WO2008127358A2 (hereafter referred to as '358 patent publication) discloses aqueous solutions for water insoluble drugs, with the use of phospholipid included in a lipid complex. The proportion of at least one phospholipid is between about 5% to about 98% of a final lipid complex (e.g., a commercially usable form) by weight. In general, the amount of at least one phospholipid is between 10% to 90% by weight of the lipid complex. In contrast, the composition of the present invention utilizes optionally phospholipids that too in very small amounts. It was found surprisingly, that the composition comprising water insoluble drugs such as the polyene antibiotics, tacrolimus, sirolimus could be effectively solubilized without the use of large amounts of phospholipids as taught by '358 patent publication.

Another prior art, namely, PCT publication WO 2008144355 A2 discloses a stable oral liquid fenofibrate formulations that include a fenofibrate component and a pharmaceutically acceptable liquid carrier that is present in an amount sufficient to solubilize the fenofibrate and that includes a lipophilic component, a surfactant component, at least one monohydric alcohol, and optionally in some embodiments an aqueous component, wherein the formulation is substantially free of an oily phase. Also included are stable liquid fenofibrate formulations including a prophylactically or therapeutically effective amount of fenofibrate and a liquid carrier present in less than 5 ml that is sufficient to maintain dissolution of the fenofibrate under ambient temperature. It may be important to note that although the formulation disclosed herein are free of oily phase, the publication teaches that the formulation can contains a lipophilic component comprising at least one triglyceride of one or more fractionated vegetable fatty acids including C to C10; a surfactant component wherein the surfactant has a HLB value of greater than 10 in amounts as high as 30 percent to about 70 percent, preferably from about 42.5 percent to about 65 percent and/or from about 46 percent to about 57.5 percent. The presence of such high amounts of surfactant may not be desirable for the above reasons discussed.

United States patent application US20040005339 (Patent application '339) claims a pharmaceutical formulation of a fibrate with improved oral bioavailability comprising a fibrate selected from fenofibrate, derivative of fenofibrate or mixtures thereof dissolved in a water miscible fibrate solubilizer selected from N-alkyl derivative of 2-pyrrolidone, ethylene glycol monoether, $C_{8-12}$ fatty acid ester of polyethylene glycol, fatty acids and combinations thereof; wherein the fibrate to solubilizer weight ratio is between about 1:1 and about 1:100. We have found out a formulation that solubilizers the fenofibrate with an amount of surfactants that is lower than the amount of fenofibrate.

In view of these problems associated with marketed formulations having very high amount of surfactants or high amounts of phospholipids, we have developed a composition that is using very, very low amounts of surfactant. We have developed a nanodispersion comprising nanoparticles having a mean size less than 300 nm dispersed in a vehicle comprising a water miscible solvent and water, said nanoparticles comprising a drug, a polymer and very low amount of surfactants and further is substantially free of phospholipids. Also the present inventors have found that molecules like fenofibrate which present lot of problems of dissolution and therefore poor bioavailability, were successfully formulated to achieve desirable dissolution when the drugs like fenofibrate were incorporated into the nanodispersion vehicle of the present invention. This results was unexpected because dissolution behaviour of drugs like fenofibrate is absolutely unpredictable.

OBJECTS OF THE INVENTION

It is the object of the present invention to provide a nanodispersion of a drug that is stable for the desired period of time before and during administration by parenteral or oral route It is the object of the present invention to provide a nanodispersion of a drug that is physically stable for the desired period of time before and during administration by parenteral route.

It is another object of the present invention to provide a nanodispersion that shows no sign of aggregation or change in appearance on storage to more than 3 hours at room temperature.

It is a further object of the present invention to provide a pre-concentrate of drug derivative which is stable chemically and shows no sign of aggregation or change in appearance on storage for at least 3 months at room temperature and which upon dilution with an aqueous liquid vehicle gives a stable nanodispersion.

SUMMARY OF THE INVENTION

A. A nanodispersion comprising nanoparticles having a mean size less than 300 nm dispersed in a vehicle comprising a water miscible solvent and water, said nanoparticles comprising one or more drugs, a polymer and a surfactant comprising a mixture of fatty acids or its salts and sterol or its derivatives or its salts.

B. A nanodispersion as described in A above, wherein the drug is selected from temsirolimus, tacrolimus, sirolimus, cyclosporine, fenofibrate or its pharmaceutically acceptable salts.

C. A nanodispersion as described in A above wherein the ratio of surfactant to the drug is about 1:5 to 1:10 and wherein the said nanodispersion is stable for at least 4 hours.

D. A nanodispersion as described in A above wherein the ratio of surfactant to drug is about 1:5 to about 1:10 and wherein the said nanodispersion is stable for 24 hours.

E. A nanodispersion as described in A above wherein the ratio of surfactant to drug is about 1:10 and the wherein the said nanodispersion is stable for 8 hours.

F. A nanodispersion as described in A above, wherein the mean size of the nanoparticles is in the range of about 10 nm to about 200 nm.

G. A nanodispersion as described in A above, wherein the water miscible solvent is selected from alcohols, glycols and its derivatives, polyalkylene glycols and its derivatives, glycerol, glycofurol and combinations thereof.

H. A nanodispersion as described in A above, wherein the water miscible solvent is selected from the group consisting of alcohol and polyethylene glycol (PEG).

I. A nanodispersion as described in A above, wherein the polymer is a water soluble polymer.

J. A nanodispersion as described in A above, wherein the water soluble polymer is selected from the group consisting of polyvinylpyrrolidone and polyethylene glycol.

K A nanodispersion as described in A above, wherein polyvinylpyrrolidone used has a molecular weight in the range of 1000 to about 50,000 and is used in the amount ranging from 0.001% w/v to 10% w/v.

L. A nanodispersion as described in A above, wherein the fatty acid or its salt is selected from the group consisting of caprylic acid, oleic acid, stearic acid and mixture thereof.

M. A nanodispersion as described in A above, wherein the sterol or its derivatives or its salts is selected from the group consisting of cholesterol, cholesteryl esters of polar acids, phytosterols, bile acids their derivative, salts and mixtures thereof.

N. Nanoparticles as described in A above wherein the polar acid is selected from the group consisting of succinic acid, hemisuccinic acid, sulfuric acid, phosphoric acid, glutamic acid and aspartic acid, boric acid.

O. A nanodispersion as described in A above, wherein the surfactant is used in an amount ranging from about 0.001% w/v to about 5.0% w/v.

P. A solution comprising one or more drugs, a polymer and a surfactant comprising a mixture of fatty acids or its salts and sterol or its derivatives or salts thereof in a water miscible solvent, which on dilution with an aqueous liquid vehicle gives a nanodispersion.

Q. Nanoparticles having a mean particle size less than 300 nms comprising one or more drugs, surfactant comprising a mixture of and fatty acid or it salts and sterol or its derivatives or its salts and a polymer.

The present invention provides a nanodispersion comprising nanoparticles having a mean particle size less than 300 nm dispersed in a vehicle comprising a water miscible solvent and water, said nanoparticles comprising one or more drugs, a polymer and a surfactant comprising a mixture of fatty acids or its salts and a sterol or its derivatives or its salts.

The present invention also provides a solution comprising one or more drugs, a polymer and a surfactant comprising a mixture of fatty acids or its salts and sterol or its derivatives or its salts in a water miscible solvent, which upon dilution with an aqueous liquid vehicle gives nanodispersion.

The present invention also provides nanoparticles having a mean particle size less than 300 nms comprising one or more drugs, surfactant comprising a mixture of sterol or its derivatives or its salts and fatty acid or its salts and a polymer.

DETAILED DESCRIPTION OF THE INVENTION

The present invention provides a nanodispersion comprising nanoparticles having a mean particle size less than 300 nm dispersed in an aqueous vehicle comprising a water miscible solvent and water, said nanoparticles comprising a drug, a polymer and a surfactant comprising a mixture of fatty acids or its salts and sterol or its derivatives or its salts.

The present invention also provides a solution comprising a drug, a polymer and a surfactant comprising a mixture of fatty acids or its salts and sterol or its derivatives or its salts in a water miscible solvent, which upon dilution with an aqueous vehicle gives nanodispersion.

The present invention also relates to nanoparticles having a mean particle size less than 300 nms comprising drug, surfactant comprising a mixture of sterol or its derivatives or its salts and fatty acid or it salts and a polymer. The nanodispersion of the present invention is devoid of toxic excipients like Cremophor and involves the use of much reduced amounts of additives (like surfactants and phospholipids) required for formulating a stable nanodispersion of drug, thus minimizing the associated toxic reactions.

The term nanoparticle as used herein means any particle having controlled dimensions of the order of nanometers. The nanoparticles as claimed in the present invention can be a polymeric nanoparticle (matrix of polymer entrapping the drug) and/or a polymeric nanovesicle (polymer stabilized nano sized vesicle encapsulating the drug.) and/or a polymeric nanocapsule (polymeric membrane surrounding drug in core) and/or nano sized particles of the drug stabilized by surfactants, and the like having mean size less than 300 nm. The particle size of the nanoparticles is determined using conventional methods of measuring and expressing particle size like Malvern particle size analysis; sieving, light scattering optical microscopy, image analysis, sedimentation and such other methods known to one skilled in the art. Particle size distribution information can be obtained from the values $D_{10}$, $D_{50}$, and $D_{90}$, such as can be generated from a Malvern particle size determination Without wishing to be bound by any theory, the applicants believe that the delivery of drug through nanodispersion comprising nanoparticles having mean size less than 300 nm, leads to enhanced internalization and accumulation of the drug in the target tumor tissues and cells. Such increased internalization levels provides a potent treatment strategy for curing tumors associated with cancer.

According to one embodiment of the present invention, the particle size of the nanoparticles is in the range of 10 nm to 275 nm. In preferred embodiments of the present invention, the particle size is less than 200 nm. In most preferred embodiments of the present invention, the particle size is in the range of 10 nm to 200 nm.

The present invention provides a nanodispersion comprising nanoparticles having a mean size less than 300 nm dispersed in a vehicle comprising a water miscible solvent and water, said nanoparticles comprising one or more active agents, a polymer and a surfactant comprising a mixture of fatty acids or its salts and sterol or its derivatives or its salts.

The present invention also provides a solution comprising one or more drugs, a polymer and a surfactant comprising a mixture of fatty acids or its salts and sterol or its derivatives or its salts in a water miscible solvent, which upon dilution with an aqueous liquid vehicle gives nanodispersion.

The nanoparticles of the present invention have a mean particle size less than 300 nms, wherein the said particles comprises one or more drugs, surfactant comprising a mixture of sterol or its derivatives or its salts and fatty acid or it salts and a polymer.

The drug derivative, as mentioned in the embodiments of the present invention, are preferably the drugs that are poorly water soluble drugs, such as sirolimus, tacrolimus, cyclosporine, fenofibrate. Preferably, these drugs are poorly water soluble and poses a problem of physically unstable due to either crystallization or aggregation problem leading to inadequate bioavailability when administered either orally or parenterally.

The nanoparticles of the present invention comprise one or more polymers. The polymer(s) that are suitable for the nanoparticles of the present invention are preferably, water soluble. Polyvinylpyrrolidone, one of the water soluble polymer is a tertiary amide polymer having linearly arranged monomer units of 1-vinyl-2-pyrrolidone, hereinafter designated PVP, and also known as Povidone. It is commercially available as a series of products having mean molecular weights ranging from about 10,000 to about 700,000. The various products are marketed according to average molecular weights designated K-values; e.g. GAF Corporation supplies PVP having the following K-values:

| K-value | Average Molecular Weight |
|---------|--------------------------|
| 15 | about 10,000 |
| 30 | about 40,000 |
| 60 | about 160,000 |
| 90 | about 360,000 |

Another supplier, BASF provides different water soluble grades of polyvinyl pyrrolidone as Kollidon with grades having for eg, molecular weight of 2000 to 3000 (Kollidon 12 PF), 7000-11,000 (Kollidon 17 PF), 28,000-34,000 (Kollidon 25), 1,000,000-1,5000,000 (Kollidon 90 F). In the embodiments polyvinylpyrrolidone is used as a water soluble polymer. The grades of polyvinylpyrrolidone suitable for the present invention include grades having a molecular weight in the range from about 1,000 to about 45,000, preferably, from about 4,000 to about 30,000. According to one embodiment of the present invention, the amount of polymer used in the nano-dispersion ranging from about 0.001% w/v to about 20% w/v. The polymer is preferably used in an amount ranging from about 0.01% w/v to about 5.0% w/v. Most preferably, it is used in an amount ranging from about 0.01% w/v to about 1.0% w/v.

The nanodispersion of the present invention comprises one or more surfactants. The term surfactant is a blend of "surface active agent". Surfactants are molecules, which comprises a water-soluble (hydrophilic) and a lipi-soluble (lipophilic) part. The surfactants that are used in the nanodispersion of the present invention comprises a mixture of fatty acid or its salts and sterol or its derivatives or its salts.

The term fatty acids includes aliphatic (saturated or unsaturated) monocarboxylic acids derived from or contained in esterified form, in an animal or vegetable fat, oil or wax. Examples of fatty acids or its salts that may be used in the compositions of the present invention include but are not limited to fatty acids or its salts having 'n' number of carbon atoms wherein 'n' ranges from about 4 to about 28. The fatty acid may be a saturated fatty acid or an unsaturated fatty acid, and their salt and combinations thereof. The saturated fatty acid and its salts may be selected from butyric acid, caproic acid, caprylic acid, capric acid, lauric acid, myristic acid, palmitic acid, stearic acid, arachidic acid, behenic acid, sodium caprylate, sodium laurate, sodium myristate, sodium palmitate and the like and/or mixtures thereof. The unsaturated fatty acid and its salts may be selected from myristoleic acid, palmitoleic acid, oleic acid, linoleic acid, alpha linolenic acid, arachidonic acid, eicosapentaenoic acid, erucic acid, docosahexaenoic acid, sodium oleate, sodium arachidonate and the like and/or mixtures thereof.

Examples of sterol or its derivative or its salts that may be used in the nanodispersion or nanoparticles of the present invention may be acid esters of sterols. The sterols that may be suitable according to the present invention include, but are not limited to, cholesterol, phytosterols, ergosterol, bile acids salts and mixtures thereof. Acid salts of cholesterol that may be used include, but are not limited to, cholesteryl sulfate, cholesterol acetate, cholesterol chloroacetate, cholesterol benzoate, cholesterol myristate, cholesterol hemisuccinate, cholesterol phosphate, cholesterol phosphate, phosphonate, borate, nitrate, cholesterol cinnamate, cholesterol crotanoate, cholesterol butyrate, cholesterol heptanoate, cholesterol hexanoate, cholesterol octanoate, cholesterol nonanoate, cholesterol decanoate, cholesterol oleate, cholesterol propionate, cholesterol valerate, dicholesteryl carbonate and the like and mixtures thereof. Phytosterols that may be used in the compositions of the present invention include sitosterol, campesterol, stigmasterol, brassicasterol and its derivatives, salts and mixture thereof. For example, Phytosterols* marketed by Sigma, U.S.A. containing bsitosterol, campesterol and dihydrobrassicasterol. Bile acids include cholic acid, chenodeoxycholic acid, deoxycholic acid, glycocholic acid, taurocholic acid, ursodeoxycholic acid and its derivatives, salts and mixture thereof. The sterols can also be esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate.

According to one embodiment of the present invention, the nanoparticles comprise a surfactant which is a mixture of sterol or its derivatives or its salts and fatty acids or its salts. In another preferred embodiment, the nanoparticles comprise of cholesterol ester of polar acids. In one preferred embodiments, the surfactant used in the nanodispersion is a mixture of caprylic acid and cholesteryl sulfate. Caprylic acid, also known as octanoic acid may be used in the embodiments in an amount ranging from about 0.001% w/v to about 5.0% w/v, more preferably from about 0.01% w/v to about 1.0% w/v and most preferably from about 0.01% w/v to about 0.5% w/v.

Cholesteryl sulfate is used in the embodiments of the present invention in an amount ranging from about 0.001% w/v to about 5.0% w/v, more preferably from about 0.01% w/v to about 1.0% w/v and most preferably from about 0.01% w/v to about 0.5% w/v.

According to another preferred embodiment, the surfactant used is selected from oleic acid and cholesteryl sulphate and/or mixtures thereof.

According to another embodiment of the present invention, the surfactant used is selected from saturated fatty acid and bile acid or bile salt and/or mixtures thereof. According to preferred embodiment, the surfactant used is selected from the group consisting of caprylic acid and sodium glycocholate or ursodeoxycholic acid and/or mixtures thereof.

Bile salts when used are employed in an amount ranging from about 0.001% w/v to about 5.0% w/v, more preferably from about 0.01% w/v to about 1.0% w/v and most preferably from about 0.01% w/v to about 0.75% w/v.

The compositions of the present invention may further comprise very low amounts of lecithins/phospholipids and/or their derivatives. By the term 'low amounts' as used herein means that the ratio of phospholipids' to drug is about 1:4 to about 1:10, that even if phospholipids are used they are used in very low amount i.e compared to the amount of drug the amount of phospholipids is very low. Generally, the prior art compositions that are liposomal, require large amounts of phospholipids compared to the amount of the drug.

In some embodiments when phospholipids are used in small amounts, the examples of such phospholipids, include, but are not limited to, lecithins natural, partially hydrogenated or hydrogenated lecithin or sphingolipids. Natural lecithins inturn are mixtures of different phospholipids. The phospholipids that may be used in the compositions of the present invention is selected from phosphatidyl choline, (dimyristoylphosphatidyl choline, dipalmitotylphosphatidyl choline, distearyloylphosphatidyl choline, dioleoylphosphatidyl choline, dilauryloylphosphatidyl choline, 1-palmitoyl-phosphatidyl choline, 1-myristoyl-2-palmitoyl phosphatidyl choline; 1-palmitoyl-2-myristoyl phosphatidyl choline, 1-stearoyl-2-palmitoyl phosphatidyl choline); phosphatidyl ethanolamine (dimyristoyl phosphatidyl ethanolamine, dipalmitoyl phosphatidyl ethanolamine, distearoyl phosphatidyl ethanolamine, lysophatidylethanolamine); sphingomyelins (brain sphingomyelin, dipalmitoyl sphingomyelin); lysolecithin; cerebrosides and the like and mixtures thereof. Further polyethylene glycol derivatives of lipids such as polyethylene glycol-distearoyl phosphatidylethanolamine (PEG-DSPE), methoxypolyethylene glycol-distearoyl phosphatidylcholine m-PEG-DSPC and the like and mixtures thereof may also be used in the compositions of the present invention. Preferably, the butylenesids that may be used in the compositions of the present invention is m-PEG-DSPE (methoxy polyethylene glycol-disteroyl phosphatidyl ethanolamine).

In one embodiment of the present invention, the phospholipid used is—mPEG-DSPE. It is used in an amount ranging from about 0.001% w/v to about 10.0% w/v, more preferably from about 0.01% w/v to about 5.0% w/v and most preferably from about 0.03% w/v to about 0.5% w/v.

The non-aqueous solvent used in the compositions of the present invention is one in which the drug is relatively soluble. The non aqueous solvent is miscible with water or aqueous solvents. Examples of such water miscible solvents used in the present invention includes, but are not limited to, alcohols such as ethanol, n-propanol, isopropanol; glycols such as ethylene glycol, propylene glycol, butylene glycol and its derivatives; polyethylene glycols like PEG 400 or PEG 3350; polypropylene glycol and its derivatives such as PPG-10 butanediol, PPG-10 methyl glucose ether, PPG-20 methyl glucose ether, PPG-15 stearyl ether; glycerol; glycofurol and the like and mixtures thereof.

In one embodiment of the present invention, the non-aqueous solvent may be selected from the group consisting of alcohols, polyethylene glycols and/or mixtures thereof. In preferred embodiment of the present invention, a mixture of ethanol and PEG (polyethylene glycol) is used as the water miscible solvent. Ethanol is used in the nanodispersion composition of the present invention in an amount ranging from about 0.001% w/v to about 5% w/v, more preferably from about 0.05% w/v to about 0.5% w/v and most preferably from about 0.1% w/v to about 0.25% w/v. Polyethylene glycols which are used preferably, include PEG-400 and PEG-3350. PEG-400 is used in the embodiments of the present invention in an amount ranging from about 0.01% w/v to about 20.0% w/v, more preferably from about 0.05% w/v to about 5.0% w/v and most preferably from about 1.0% w/v to about 2.5% w/v. PEG-3350 is used, in the embodiments of the present invention in an amount ranging from about 0.001% w/v to about 10.0% w/v, more preferably from about 0.05% w/v to about 5.0% w/v and most preferably from about 0.1% w/v to about 3% w/v.

Generally, it is desirable that a drug pre-concentrate i.e the solution upon dilution with the aqueous vehicle gives a nanodispersion that remains stable for at least about 4 hours. This time is the time during which the nanodispersion may be administered to the patient in the form of infusion. Thus, it is always desirable to achieve minimum of 4 hours stability of the nanodispersion of the present invention. The vehicle may further comprise about 5% to about 10.0% w/v dextrose solution in water for injection or any other pharmaceutically acceptable intravenous aqueous liquid vehicle and mixtures thereof. One of the embodiments of the present invention wherein drug is a hydrophobic drug such as temsirolimus, sirolimus, the aqueous vehicle further comprises 5% dextrose solution in order to improve this stability but additional stabilizers may also be present in the aqueous phase. Examples of such stabilizers are hetastarch, dextran, sodium hyaluronate, glutathione, ornithin-L-aspartate and the like and mixtures thereof.

In one embodiment, when the solution of the present invention as claimed may be designed for oral administration. The solution, also referred to as pre-concentrate may be filled into hard or soft gelatin capsules. Upon oral administration, the solution is dispersed in the aqueous medium and therefore, the drugs like fenofibrate are dispersed in the form of nanoparticles having a particle size in the nanometer range, sufficient to provide adequate dissolution. The nanodispersion vehicle allows the drug particles to remain in the dispersion, physically stable for a desired period of time, for example, 1 hour to 3 hours which is sufficient for the drug to be absorbed into the body, when the nanodispersion is administered orally.

In another embodiment, the solution may be dried to form nanoparticles. The nanoparticles may be formulated along with pharmaceutically acceptable excipients to form solid dosage form like tablet, granules, pellets.

The nanodispersion of drug of the present invention may be typically prepared by any one of the processes listed below:

1) The therapeutically active ingredient (and/or other agents), polymer(s) and surfactant(s) selected from fatty acids or its salts, sterol or its derivatives or its salts and mixtures thereof is dissolved in water misbicle solvent such as ethanol and/or PEG, along with stirring and heating to obtain a concentrated solution of the drug. The solution so obtained is filtered through a membrane filter. To this solution, an aqueous liquid vehicle (5% dextrose solution) is added slowly and the mixture is shaken/agitated, thus leading to the formation of the nanodispersion of the present invention. The nanodispersion so formed is optionally homogenized and/or sonicated, filtered or lyophilized. The lyophilized powder of the medicament can be reconstituted with the aqueous medium, reforming nanodispersion of the present invention, prior to administration to the patients.

2) The drug, polymer(s) and surfactant(s) selected from fatty acids or its salts, sterol or its derivatives or its salts and mixtures thereof is dissolved in water miscible solvent such as ethanol and/or PEG along with stirring and heating to obtain a concentrated solution of the drug. The solution so obtained is filtered through a membrane filter and is added to an aqueous medium (5% dextrose solution) and the mixture is shaken/agitated, thus leading to the formation of the nanodispersion of the present invention. The nanodispersion so formed is optionally homogenized and/or sonicated, filtered or lyophilized. The lyophilized powder of the medicament can be reconstituted with the aqueous medium, reforming nanodispersion of the present invention, prior to administration to the patients.

3) drug and surfactant(s) comprising a mixture of fatty acids or its salts and sterol or its derivatives or its salts is dissolved in water miscible solvent such as ethanol and/or PEG by slightly warming at 40° C. in a round bottomed flask, and the solvent is evaporated to form a thin film of the drug. The polymer(s) is dissolved in required quantity of an aqueous medium and this solution is added to the film with gentle agitation and shaking for 3-4 hours, thus leading to the formation of the nanodispersion of the present invention. The nanodispersion so formed is optionally homogenized and/or sonicated, filtered and lyophilized. The lyophilized powder of the medicament can be reconstituted with the aqueous medium, reforming nanodispersion of the present invention prior to administration to the patients.

As the nanodispersion of the present invention is a colloidal nanodispersion of drug comprising nanoparticles having a mean size less than 300 nm, they were analyzed for physical and chemical stability. It was observed that the particles do not aggregate upon storage at room temperature for about 8 hours to 24 hours and the nanodispersion shows no sign of change in appearance, inferring that the nanodispersion is stable for the desired period of time before and during administration.

Also, when a solution of a drug and/or other agents in water miscible solvent was tested, it was observed that the solution remains physically and chemically stable for at least a time period required for administration of the composition either orally or parenteral, with no significant change in assay of the drug and no substantial aggregation or change in appearance of the formulation. The observations are illustrated in the upcoming examples.

The nanodispersion of the present invention can be provided as a kit having two or more containers, for example two containers, wherein the first container comprising a solution of a drug, a polymer and a surfactant comprising a mixture of fatty acids or its salts and sterol or its derivatives or its salts in a water miscible solvent, and a second container comprising an aqueous liquid vehicle, such that on addition of contents of second container to the contents of the first container or vice versa, with mild agitation or shaking, results in the formation of nanodispersion of the present invention and is suitable for intravenous administration. An additional container may contain a third component for mixing prior to formation of drug nanodispersion or after nanodispersion of the said drug is formed.

The present invention also provides a kit having two containers, the first container comprising a lyophilized form of the nanodispersion and a second container comprising an aqueous liquid vehicle such that prior to administration to the patients, the contents of second container can be added to the contents of the first container or vice versa with mild agitation or shaking, resulting in the formation of nanodispersion of the present invention.

Administering the nanodispersion of the present invention to patients in need thereof, will provide an efficient method of treatment of various types of cancers known in the art.

While the present invention is disclosed generally above, additional aspects are further discussed and illustrated with reference to the examples below. However, the examples are presented merely to illustrate the invention and should not be considered as limitations thereto.

EXAMPLE I

| Ingredients | % by weight/weight |
|---|---|
| Drug (Temsirolimus or Sirolimus) | 6 |
| Caprylic Acid | 0.5 |
| Sodium Cholesteryl Sulfate | 0.4 |
| Povidone (K-12) | 5 |
| Dehydrated Alcohol | 6 |
| Polyethylene Glycol 400 | qs to 100 |

Drug, cholesteryl sulfate, caprylic acid and PVP K-12 were weighed accurately in a glass vessel. Contents were dissolved in the required quantity of absolute ethanol and PEG-400 with stirring to obtain a concentrated drug solution. The solution was filtered through 0.2µ PVDF membrane filter. The required amount of the preconcentrate was dispersed in the dextrose solution (5% w/v) (50 ml) with gentle shaking to get a transparent to transluscent nanodispersion of drug having dilution of 0.1 mg/ml. Nanodispersion was analyzed for the following tests: Appearance, pH (Mettler Toledo-seven easy, pH Meter) and Particle size (Nano-ZS, Malvern Particle size analyzer), described below. The pre-concentrate so prepared was found to be clear colorless slightly viscous solution. It was mixed with the aqueous phase such as dextrose solution to achieve a nanodispersion. The stability of the nanodispersion in terms of the particle size of the dispersed particles was determined initially as well as on storage for few hours.

| | Time point of observation | Temsirolimus Nanodispersion | Sirolimus Nanodispersion |
|---|---|---|---|
| Parameter observed | 0 hr | Almost Clear to Translucent Dispersion | Almost Clear to Translucent Dispersion |
| | 48 hr | Almost Clear to Translucent Dispersion | Almost Clear to Translucent Dispersion |
| Particle Size | 0 h | 81.5 nm, 0.192 | 125 nm, 0.127 |
| | 2 h | 82 nm, 0.161 | 128 nm, 0.149 |
| | 4 h | 99.7 nm, 0.209 | ND |
| | 8 h | 102 nm, 0.211 | 129 nm, 0.169 |
| | 24 h | 112 nm, 0.369 | 138 nm, 0.297 |
| | 48 h | 135 nm, 0.304 | 148 nm, 0.287 |
| pH | 0 h | 4.71 | 4.60 |
| | 48 h | 4.77 | 4.62 |
| Zeta potential | | −29.1 mV | −40.7 mV |
| Osmolality | | 316 mOsm | 309 mOsm |
| % Transmittance at 650 nm | | 95.00% | 94.87% |

| Time point of observation | Temsirolimus Nanodispersion | Sirolimus Nanodispersion |
|---|---|---|
| Absorbance at 420 nm | 0.071 A<br>Stable For 48 h, very slight settlement, without any change in appearance. | 0.093 A<br>Stable For 48 h, very slight settlement, without any change in appearance. |

EXAMPLE 2

| Ingredients | % by weight/weight |
|---|---|
| Cyclosporine | 3 |
| Caprylic Acid | 0.25 |
| Sodium Cholesteryl Sulfate | 0.2 |
| Povidone (K-17) | 2.5 |
| Dehydrated Alcohol | 6 |
| Polyethylene Glycol 400 | Qs to 100 |

Drug, cholesteryl sulfate, caprylic acid and PVP K-17 were weighed accurately in a glass vessel. Contents were dissolved in the required quantity of absolute ethanol and PEG-400 with stirring to obtain a concentrated drug solution. The solution was filtered through 0.2μ PVDF membrane filter. Required amount of the preconcentrate was dispersed in the Dextrose solution (5% w/v) (50 ml) with gentle shaking to get a transparent to translucent nanodispersion of drug having dilution of 0.5 mg/ml. Nanodispersion was analyzed for the following tests: Appearance, pH (Mettler Toledo-seven easy, pH Meter) and Particle size (Nano-ZS, Malvern Particle size analyzer), described below.

The pre-concentrate so prepared is found to be clear colorless slightly viscous solution. It was mixed with the aqueous phase such as dextrose solution to achieve a nanodispersion. The stability of the nanodispersion in terms of the particle size of the dispersed particles was determined initially as well as on storage for few hours.

| Parameters | | Cyclosporine Nanodispersion |
|---|---|---|
| Description | 0-3 h | Whitish translucent Dispersion |
| Particle Size | 0 h | 214 nm, 0.099 |
| | 1 h | 248 nm, 0.076 |
| | 3 h | 303 nm, 0.164 |
| | 5 h | 1240 nm, 0.210 |
| pH | | 3.56 |
| Zeta potential | | −52.5 mV |
| Osmolality | | 318 mOsm |
| | | Stable For 3 h, At 5 hr very sight settlement observed. |

EXAMPLE 3

| Ingredients | Quantity % w/w |
|---|---|
| Fenofibrate | 17.5 |
| HPMC (NE coat) | 8.75 |
| Povidone K17 | 10.675 |
| Sodium Cholesteryl Sulfate | 2.6875 |
| Caprylic acid | 2.325 |
| PEG 3350 q.s to | 100 |
| Ethanol q.s. | q.s. |

All the ingredients were dissolved in ethanol with heating if required. The ethanol was evaporated. The dry mixture was then melted and water was added at 60° C. with silverson homogenizer. The nanodispersion with mean particle size<1000 nm (~300 to 1000 nm) is formed. The nanodispersion was spray dried. The spray dried powder was reconstituted in water to obtain nanodispersion of mean particle size 900 nm to 1700 nm. The dissolution of 50 mg fenofibrate equivalent spray dried powder was >80% within 15 min and >90% within 30 min.

EXAMPLE 4

| Ingredients | Quantity (% w/w) | Quantity (mg/g) |
|---|---|---|
| Fenofibrate | 14.5 | 145 |
| Caprylic Acid | 12.0 | 120 |
| Sodium Cholesteryl Sulfate | 1.0 | 10 |
| Povidone (K-12) | 1.2 | 12 |
| Dehydrated Alcohol | 14.5 | 145 |
| Polyethylene Glycol 400 | qs to 100 | qs to 1000 |

Drug, Sodium cholesteryl sulfate, caprylic acid, and Povidone (K-12) were weighed accurately in a glass vessel. Contents were dissolved in the required quantity of Absolute Alcohol and PEG-400 with stirring to obtain a clear concentrated drug solution. The solution was filtered through 0.2μ PVDF membrane filter. The pre-concentrate so prepared was found to be clear colorless slightly viscous solution. The required amount of the preconcentrate was dispersed in the dextrose solution (5% w/v) with gentle shaking to get a white translucent nanodispersion of drug having dilution of 5.0 mg/ml. Nanodispersion was analyzed for the following tests: Appearance, pH (Mettler Toledo-seven easy, pH Meter) and Particle size (Nano-ZS, Malvern Particle size analyzer), described below. The stability of the nanodispersion in terms of the particle size of the dispersed particles was determined initially as well as on storage ie. after 1 h.

| Parameters | Timepoints | Observation & Results |
|---|---|---|
| Description | Initial | White Translucent Dispersion |
| | 1 h | White Translucent Dispersion |
| Particle Size | Initial | 244 nm, 0.038 (142-459) |
| | | ($D_{10}$-175, $D_{50}$-250, $D_{90}$-359) |
| | 1 h | 533 nm, 0.216 (192-615) |
| | | ($D_{10}$-309, $D_{50}$-432, $D_{90}$-553) |
| pH | Initial | 4.26 |
| | 1 h | 4.20 |
| Zeta (Initial) | | −25.1 mV |
| Osmolality (Initial) | | 397 mOsm |

EXAMPLE 5

| Ingredients | Quantity (% w/w) | Quantity (mg/g) |
|---|---|---|
| Tacrolimus | 6 | 60 |
| Caprylic Acid | 0.5 | 5.0 |
| Sodium Cholesteryl Sulfate | 0.40 | 4.0 |
| Povidone (K-17) | 5.0 | 50 |
| Dehydrated Alcohol | 6 | 60 |
| Polyethylene Glycol 400 | qs to 100 | qs to 1000 |

Drug, Sodium cholesteryl sulfate, caprylic acid, and Povidone (K-17) were weighed accurately in a glass vessel. Contents were dissolved in the required quantity of Absolute Alcohol and PEG-400 with stirring to obtain a clear concentrated drug solution. The solution was filtered through 0.2μ PVDF membrane filter. The pre-concentrate so prepared was found to be clear colorless slightly viscous solution. The required amount of the preconcentrate was dispersed in the dextrose solution (5% w/v) with gentle shaking to get a white transluscent nanodispersion of drug having dilution of 0.1 mg/ml. Nanodispersion was analyzed for the following tests: Appearance, pH (Mettler Toledo-seven easy, pH Meter) and Particle size (Nano-ZS, Malvern Particle size analyzer), described below.

The stability of the nanodispersion in terms of the particle size of the dispersed particles was determined initially as well as on storage i.e after 24 h.

| Parameters | Timepoints | Observation & Results |
|---|---|---|
| Description | Initial | White Translucent Dispersion |
|  | 24 h | White Translucent Dispersion |
| Particle Size | Initial | 289 nm, 0.191(142-531) |
|  |  | ($D_{10}$-193, $D_{50}$-277, $D_{90}$-406) |
|  | 24 h | 217 nm, 0.066(122-459) |
|  |  | ($D_{10}$-155, $D_{50}$-224, $D_{90}$-328) |
| pH | Initial | 4.4 |
|  | 24 h | 4.77 |
| Zeta (Initial) |  | −43.1 mV |
| Osmolality (Initial) |  | 387 mOsm |

EXAMPLE 6

| Ingredients | Quantity (% w/w) | Quantity (mg/g) |
|---|---|---|
| Brinzolamide | 3 | 30 |
| Caprylic Acid | 0.67 | 6.7 |
| Sodium Cholesteryl Sulfate | 0.67 | 6.7 |
| Povidone (K-17) | 7.5 | 75 |
| Dehydrated Alcohol | 9 | 90 |
| Polyethylene Glycol 400 | qs to 100 | qs to 1000 |

Drug, Sodium cholesteryl sulfate, caprylic acid, and Povidone (K-17) were weighed accurately in a glass vessel. Contents were dissolved in the required quantity of Absolute Alcohol and PEG-400 with stirring and by heating at 60° C. to obtain a clear concentrated drug solution. The solution was filtered through 0.2μ PVDF membrane filter. The pre-concentrate so prepared was found to be clear colorless to pale yellow slightly viscous solution. The required amount of the preconcentrate was dispersed in 0.25% Hypromellose (HPMC) solution with gentle shaking to get a nanodispersion of drug having dilution of 1.0 mg/ml. Nanodispersion was analyzed for the following tests: Appearance, pH (Mettler Toledo-seven easy, pH Meter) and Particle size (Nano-ZS, Malvern Particle size analyzer), described below. The particle size of the nanodispersion was determined initially as well as on storage till 2 h.

| Parameters | Timepoints | Observation & Results |
|---|---|---|
| Description | Initial | Almost Clear colorless |
|  | 2 h | solution |
| Particle Size | Initial | 24.8 nm, 0.473 (2.01-32.1) |
|  |  | ($D_{10}$-2.60, $D_{50}$-3.82, $D_{90}$-13.6) |
|  | 2 h | 26.0 nm, 0.551 (7.53-58.8) |
|  |  | ($D_{10}$-9.67, $D_{50}$-14.5, $D_{90}$-24.7) |
| pH | Initial | 5.9 |
|  | 2 h | — |

The invention claimed is:
1. A solution consisting of:
   (a) a drug,
   (b) a polymer selected from the group consisting of polyvinylpyrrolidone, polyglutamic acid or its salt and hyaluronic acid or its salt,
   (c) a surfactant consisting of a mixture of caprylic acid or its salts and cholesteryl sulphate or its salt, and
   (d) a water miscible solvent selected from the group consisting of alcohol, polyethylene glycol and polypropylene glycol;
   such that dilution of the solution with an aqueous liquid vehicle or vice versa, with agitation or shaking, results in the formation of a nanodispersion that remains stable for at least 4 hours with no aggregation or crystallization of the said drug.

2. The solution as claimed in claim 1, wherein the weight ratio of the surfactant to the drug is in the range of about 1:5 to 1:10.

3. The solution as claimed in claim 1, wherein the weight ratio of the surfactant to the drug is about 1:6.

4. The solution as claimed in claim 1, wherein the polymer is polyvinylpyrrolidone having a molecular weight in the range of about 1000 to about 50,000, and present in an amount ranging from 0.001% w/v to 10% w/v.

5. The solution as claimed in claim 1, wherein the aqueous liquid vehicle comprises about 5% w/v to about 10% w/v dextrose solution.

6. The solution as claimed in claim 5, wherein the nanodispersion formed upon dilution of the solution with an aqueous liquid vehicle comprises caprylic acid in an amount ranging from about 0.01% w/v to about 0.5% w/v.

7. The solution as claimed in claim 5, wherein the nanodispersion formed upon dilution of the solution with an aqueous liquid vehicle comprises cholesteryl sulphate in an amount ranging from about 0.01% w/v to about 0.5% w/v.

8. The solution as claimed in claim 5, wherein the nanodispersion formed upon dilution of the solution with an aqueous liquid vehicle comprises ethanol in an amount ranging from about 0.001% w/v to about 5% w/v and polyethylene glycol in an amount ranging from about 0.05% w/v to about 5.0% w/v.

9. A kit comprising two containers, wherein
a first container comprises a solution consisting of:
   (a) a drug,
   (b) a polymer selected from the group consisting of polyvinylpyrrolidone, polyglutamic acid or its salt and hyaluronic acid or its salt, (c) a surfactant consisting of a mixture of caprylic acid or its salts and cholesteryl sulphate or its salt, and
(d) a water miscible solvent selected from the group consisting of alcohol, polyethylene glycol and polypropylene glycol; and a second container comprises an aqueous liquid vehicle;

such that addition of the contents of the first container to the second container and vice versa with agitation or shaking results in the formation of a nanodispersion that remains stable for at least 4 hours with no aggregation or crystallization of the drug.

10. A nanodispersion of a drug that remains stable for at least 4 hours with no aggregation or crystallization of a drug, wherein the nanodispersion is formed by addition of an aqueous liquid vehicle to a solution consisting of:
(a) a drug,
(b) a polymer selected from the group consisting of polyvinylpyrrolidone, polyglutamic acid or its salt and hyaluronic acid or its salt,
(c) a surfactant consisting of a mixture of caprylic acid or its salts and cholesteryl sulphate or its salt, and
(d) a water miscible solvent selected from the group consisting of alcohol, polyethylene glycol and polypropylene glycol;

or vice versa, with agitation or shaking.

* * * * *